United States Patent [19]

Lemieux

[11] 4,191,185
[45] Mar. 4, 1980

[54] CATHETER ASSEMBLY

[75] Inventor: Francis P. Lemieux, Morristown, N.J.

[73] Assignee: Johnson & Johnson, New Brunswick, N.J.

[21] Appl. No.: 830,933

[22] Filed: Sep. 6, 1977

[51] Int. Cl.² ........................ A61M 5/00; A61M 25/00
[52] U.S. Cl. .................................... 128/214.4; 128/348
[58] Field of Search ................ 128/214.4, 221, 348, 128/DIG. 16

[56] References Cited

U.S. PATENT DOCUMENTS

| 3,234,944 | 2/1966 | Stevens | 128/221 |
| 3,454,006 | 7/1969 | Langdon | 128/214.4 |
| 3,469,579 | 9/1969 | Hubert | 128/214.4 |
| 3,472,227 | 10/1969 | Burke | 128/221 |
| 3,720,210 | 3/1973 | Diettrich | 128/214.4 |
| 3,802,433 | 4/1974 | Raven | 128/214.4 |
| 4,044,765 | 8/1977 | Kline | 128/214.4 |

Primary Examiner—Dalton L. Truluck

[57] ABSTRACT

A catheter assembly has a hub with an axial opening extending therethrough, the distal end of the opening having a standard size to accommodate the proximal section of a catheter securement insert having a passageway therethrough in alignment with the axial opening. A catheter is secured within the passageway in fluid communication with the axial opening.

5 Claims, 6 Drawing Figures

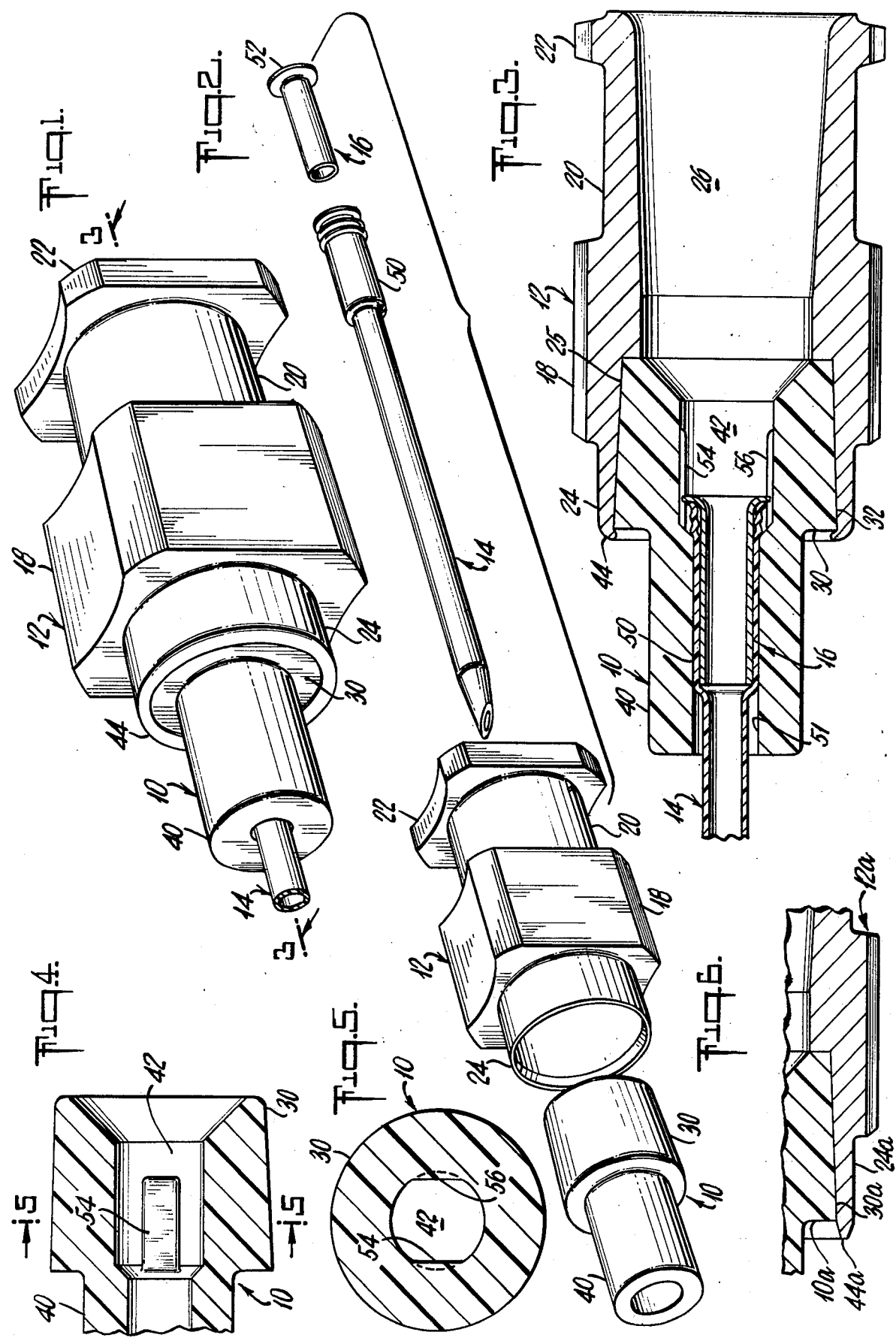

CATHETER ASSEMBLY

BACKGROUND OF THE INVENTION

This invention relates to a catheter assembly and, more particularly, to a unique hub and catheter securement insert structure that greatly facilitates the fabrication of the catheter assembly and provides flexibility in the use of a single hub element.

Catheter assemblies utilizing a relatively long flexible hollow plastic catheter for insertion into the vein of a patient have long been utilized for the infusion of intravenous fluids and other medication. A catheter assembly of the type contemplated by the subject invention is illustrated and described in U.S. Pat. No. 3,094,122. This patent very clearly describes the structure of one type of catheter to which this invention relates and thoroughly describes and illustrates the utilization of such a catheter. Another infusion catheter assembly is illustrated and described in U.S. Pat. No. 3,802,433. This patent discloses that a flexible plastic catheter may be secured to the internal bore of a catheter hub by inserting a metal sleeve internally of the proximal end of the catheter to expand that end against the internal surface of the catheter hub. Many such approaches for the attachment of a plastic catheter to a plastic or metal hub have been previously suggested. However, all prior approaches for solving this problem have been very limited in nature in that each catheter hub configuration has been intended to accommodate only a single gauge catheter.

This has been particularly troublesome when the catheter assembly was fabricated with a metal hub. Because the catheter was usually attached to the metal hub in the manner illustrated in U.S. Pat. No. 3,094,122, a separate hub structure was required for each catheter gauge. Obviously, this necessitated the stocking of a large number of metal hubs and, thus, created unwieldy raw material inventory problems. In addition, the cost of procuring hubs in a plurality of sizes was excessive.

Therefore, it has been desirable for many years to provide a catheter assembly in which the main component of the hub could be standardized at a single size and yet could be utilized with a variety of catheter gauges.

SUMMARY OF THE INVENTION

The present invention provides a catheter assembly which utilizes a unique hub structure which may be used with a plurality of catheter gauges. As used herein, the word "proximal" shall mean that portion of an element which, during normal use, would be at a location nearest the operator. For example, during the introduction of an infusion catheter into a patient, the hub would be at the proximal end of the catheter assembly. Whereas, the point of the catheter would be at a location remote from the proximal end and this end shall be defined in this specification as the "distal" end.

The primary structural feature that provides the flexibility for the unique catheter assembly of this invention is that the catheter hub has, in effect, been divided into two structural elements. The first of these elements is a more or less standard hub member which has an axial opening extending therethrough. At the distal end of the hub the opening is adapted to receive the proximal end of the second hub element which is in the form of a catheter securement device or insert which is positioned and secured within the distal end of the opening. It will thus be appreciated that the distal end of the hub opening and the proximal end of the insert may be standardized so that a single hub may be utilized with a plurality of catheter securement inserts.

In order to enable the catheter securement inserts to be utilized with a plurality of catheter gauges, the inserts are provided with passageways that extend completely therethrough in alignment with the axial opening in the catheter assembly hubs. The passageways are dimensioned to accommodate various gauges of catheters which are secured within the passageway by a suitable locking device.

Thus, it will be evident from the foregoing that a unique catheter assembly has been provided that permits the utilization of a single catheter assembly hub in combination with catheter securement inserts that may accommodate a plurality of catheter gauges. This assembly permits the reduction from inventory of a large number of different hub sizes and provides a unique catheter assembly that is relatively easy to fabricate.

Another important aspect of the present invention is that the use of a specific catheter securement insert for each catheter gauge permits the insert to be color-coded for identification purposes. This greatly facilitates the handling of the various parts during manufacture and eliminates inadvertent mixing of the various catheter sizes.

BRIEF DESCRIPTION OF THE DRAWING

The invention will be particularly described with reference to the following detailed description of the preferred embodiment of the invention when considered together with the attached drawing, in which:

FIG. 1 is a perspective view of the catheter assembly with the catheter tip broken away;

FIG. 2 is a perspective view illustrating the assembly of the various parts of the catheter assembly;

FIG. 3 is a cross sectional view taken along line 3—3 in FIG. 1;

FIG. 4 is a cross sectional view of the proximal section of the catheter securement insert;

FIG. 5 is a cross sectional view taken along line 5—5 of FIG. 4; and

FIG. 6 is a cross sectional view of the distal end of the catheter assembly hub illustrating another embodiment of the present invention.

DESCRIPTION OF THE PREFERRED EMBODIMENTS

An infusion catheter assembly of the type contemplated by the present invention is illustrated and described in U.S. Pat. No. 3,094,122. This type of catheter assembly is normally utilized in combination with an introducer needle that is positioned within the plastic catheter during the introduction of the catheter into the vein of a patient and then removed therefrom so that a syringe or other fluid connector may be coupled to the hub portion of the catheter assembly. This type of catheter assembly has been used for a number of years and is now widely accepted as the device of choice for long dwelling infusion.

Referring first to FIG. 2, the four component parts of the unique catheter assembly of the present invention are illustrated in an assembly drawing. These component parts are a catheter securement insert 10, a catheter assembly hub 12, a flexible hollow plastic catheter 14 and a catheter locking member in the form of a sleeve 16.

Hub 12 comprises a generally square gripping block 18 which may be firmly held by the operator during the introduction of the catheter into the vein of a patient. Extending proximally of block 18 is a generally cylindrically shaped member 20 having an outwardly directed flange 22 at its extreme proximal end. Flange 22 is utilized for locking the hub to a syringe or other fluid connector. The internal surface of member 20 has a luer taper to accommodate the male projection of a syringe nozzle or other connector. Distal end 24 of the hub extends from the other side of block 18 and preferably has a generally cylindrical configuration. The internal surface 25 of distal end 24 is tapered outwardly to provide a press-fit between the hub and insert 10 as hereinafter described. An axial opening 26 extends completely through the various parts of hub 12. Although the material of hub 12 is not critical, it is very desirable that the hub be constructed of a material that is biologically compatible and that provides chemical resistance with respect to body fluids and to the infusion fluids normally utilized with this type of medical infusion device. It has been found that a metal hub performs exceptionally well with this invention and the preferred metal is a nickel plated or chrome plated brass. Other suitable metals for use in the fabrication of hub 12 are easily formable aluminum, stainless steel and zinc.

Referring to FIG. 3, the proximal section 30 of catheter securement device 10 is shown firmly seated and secured within distal end 24 of axial opening 26. The external surface 32 of proximal section 30 has an exterior taper which matches the taper of internal surface 25 and thereby forms a press-fit between the hub and insert 10 which firmly locks the two components together.

Insert 10 also comprises a distal section 40 which extends outwardly beyond the end of distal end 24. Passageway 42 extends completely through insert 10 and, in the assembled condition illustrated in FIG. 3, is in alignment with opening 26.

In the preferred embodiment of this invention, as illustrated in FIG. 3, at least a part of the extreme tip 44 of distal end 24 is turned inwardly to securely lock proximal section 30 of insert 10 within opening 26. Other measures may be taken, such as, a staking operation, which would provide even further security with respect to the attachment between the various components of the catheter assembly. However, it has been found, as illustrated in FIG. 6, that the hub and insert, when properly dimensioned, will securely remain together without turning tip 44 inwardly and without any further securement measures. In the FIG. 6 embodiment, hub 12a is shown with a distal end 24a into which the proximal section 30a of insert 10a has been positioned. Extreme tip 44a of distal end 24a is illustrated in an unturned position and, as stated above, this configuration has been found to be an adequately operable embodiment.

Referring to FIG. 3, the proximal portion 50 of catheter 14 is secured within passageway 42 and firmly retained therein by sleeve 16 which is positioned within the proximal end of the lumen of catheter 14. By forcing sleeve 16 into the lumen of catheter 14, it effects an expansion of proximal end 50 into contact with the internal surface 51 of distal section 40 of insert 10 thereby locking the insert and the catheter together to prevent axial movement therebetween. As illustrated in FIGS. 2 and 3, sleeve 16 is outwardly tapered at its proximal end to form a flange 52 which acts to securely position sleeve 16 relative to the locking ribs 54 and 56 which are integral with the internal wall of proximal section 30 (see FIGS. 3, 4 and 5). It will be noted from FIG. 3, that the extreme proximal end of catheter 14 is somewhat compacted during the insertion of sleeve 16 within the catheter lumen and thereby provides additional security against the axial displacement of the catheter with respect to catheter securement insert 10.

Because it is intended that the catheter assembly of the present invention be utilized in conjunction with the human body, it is desirable that all of the component parts of the catheter assembly be constructed from materials that are compatible with body tissue and fluids. There are many materials, both metal and plastic, that meet these requirements and, therefore, it is not intended that this invention be limited to any specific structural material. For example, because the catheter securement insert is intended to be utilized with a specific catheter gauge it is desirable from an economic, aesthetic and functional point of view that the insert be made from a plastic material. This also will enable the insert to be color-coded to indicate the specific catheter gauge which is identified by that color. This greatly facilitates in-process part identification and thereby reduces any inconsistencies in the finished assembly. The presently preferred plastic material from which insert 10 may be made is an alloy of polycarbonate and ABS which is available commercially from the Borg-Warner Corporation under its trademark Cycoloy 800. Other plastic materials which may preferably be color-coded and molded with dimensional stability are suitable for use in the fabrication of insert 10. A catheter constructed from fluorinated ethylene propylene and a stainless steel sleeve have been found to function very effectively with the subject invention.

It will be apparent from the foregoing description that a unique catheter assembly is provided by the subject invention. The unique catheter assembly provides a catheter hub that may be utilized with a variety of catheter gauges when such catheters are firmly connected to the catheter hubs by a uniquely designed catheter securement insert. This structural arrangement requires that only a single catheter hub be maintained in inventory and, thus, greatly reduces the inventory and eliminates the possibility of erroneously selecting an improperly sized hub.

In addition, the unique structure permits the catheter securement inserts to be color-coded for each specific catheter gauge and, thus, facilitates in-process handling and inspection of the raw materials.

What is claimed is:

1. A catheter assembly comprising: a hub having an axial opening therethrough; catheter securement means including a color-coded plastic insert having a proximal section secured within the distal end of said axial opening and a distal section extending outwardly therefrom, said insert having a passageway extending therethrough in alignment with said axial opening; and a flexible hollow plastic catheter having a proximal portion secured within said passageway of said insert only, there being no direct contact between said catheter and said hub, said catheter having a distal portion extending beyond the distal end of said insert, said proximal portion of said catheter being secured within said passageway in fluid communication with said axial opening by an internal sleeve, having expanded only said proximal portion outwardly into locking contact with the internal surface of said distal section of said insert.

2. The catheter assembly of claim 1, wherein the internal surface of said distal end of said hub is tapered outwardly and the external surface of said proximal section within said axial opening has a matching taper to provide a press-fit therebetween.

3. The catheter assembly of claim 2, wherein at least a part of the extreme tip of said distal end of said hub is turned inwardly to securely lock said proximal section within said opening.

4. The catheter of claim 1, wherein said sleeve is tapered outwardly at its proximal end to form a flange and wherein the internal wall of said insert surrounding said passageway includes locking ribs, said flange being engaged to said ribs to provide secure locking of said sleeve to said insert.

5. The catheter assembly of claim 1 wherein said hub is metal.

* * * * *